(12) United States Patent
Chen et al.

(10) Patent No.: US 11,617,391 B2
(45) Date of Patent: Apr. 4, 2023

(54) ELECTRONIC ATOMIZING DEVICE AND ATOMIZER AND SUCTION NOZZLE ASSEMBLY THEREOF

(71) Applicant: SHENZHEN SMOORE TECHNOLOGY LIMITED, Shenzhen (CN)

(72) Inventors: Shouhao Chen, Shenzhen (CN); Fuxuan Li, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 345 days.

(21) Appl. No.: 16/869,591

(22) Filed: May 8, 2020

(65) Prior Publication Data
US 2020/0352228 A1     Nov. 12, 2020

(30) Foreign Application Priority Data

May 8, 2019 (CN) .......................... 201920673346.6

(51) Int. Cl.
*A24F 40/40* (2020.01)
*A61M 15/00* (2006.01)
(Continued)

(52) U.S. Cl.
CPC ............... *A24F 40/10* (2020.01); *A24C 5/01* (2020.01); *A24F 40/40* (2020.01); *A61M 11/04* (2013.01);
(Continued)

(58) Field of Classification Search
CPC ............ A24F 40/10; A24F 40/40; A24C 5/01; A61M 11/04; A61M 11/042;
(Continued)

(56) References Cited

U.S. PATENT DOCUMENTS

2017/0325289 A1* 11/2017 Liu ....................... H05B 1/0227
2018/0235277 A1*  8/2018 Lin .......................... H05B 3/46
(Continued)

FOREIGN PATENT DOCUMENTS

CN          208403263         1/2019
CN          209788471        12/2019

OTHER PUBLICATIONS

"Office Action of Canada Counterpart Application", dated Mar. 15, 2022, p. 1-p. 7.
(Continued)

*Primary Examiner* — Abdullah A Riyami
*Assistant Examiner* — Thang H Nguyen
(74) *Attorney, Agent, or Firm* — JCIP Global Inc.

(57) ABSTRACT

The present invention relates to an electronic atomizing device, an atomizer and a suction nozzle assembly thereof. The suction nozzle assembly includes a fixing base, a suction nozzle, and a connecting member. The suction nozzle includes a first end and a second end away from the first end. One end of the connecting member is mounted to the suction nozzle, another end is mounted to the fixing base, such that the suction nozzle is disposed on the fixing base via the first end, and is capable of rotating relative to the fixing base. The suction nozzle can rotate relative to a power supply assembly in the electronic atomizing device, therefore an operation switch of the power supply assembly can be rotated from an initial position to an operation position convenient for an operation.

16 Claims, 6 Drawing Sheets

(51) Int. Cl.
  *A61M 11/00*   (2006.01)
  *A24F 40/10*   (2020.01)
  *A61M 15/06*   (2006.01)
  *A24C 5/01*    (2020.01)
  *A61M 11/04*   (2006.01)

(52) U.S. Cl.
  CPC ..... *A61M 15/06* (2013.01); *A61M 2205/8206* (2013.01)

(58) Field of Classification Search
  CPC .............. A61M 15/0021; A61M 15/06; A61M 2202/0468; A61M 2205/8206
  See application file for complete search history.

(56) References Cited

U.S. PATENT DOCUMENTS

| | | | |
|---|---|---|---|
| 2019/0230991 A1* | 8/2019 | Liu | A24F 40/30 |
| 2019/0261690 A1* | 8/2019 | Lin | H01M 50/213 |
| 2019/0269177 A1* | 9/2019 | Liu | A24F 40/485 |
| 2020/0037662 A1* | 2/2020 | Richmond | H05B 1/0227 |

OTHER PUBLICATIONS

"Office Action of Counterpart Canada Application No. 3,080,608", dated Sep. 29, 2022, p. 1-p. 7.
"Response to Office Action of Counterpart Canada Application No. 3,080,608", dated Jul. 11, 2022, p. 1-p. 19.
"Office Action of Counterpart Canada Application No. 3,080,608", dated Mar. 15, 2022, p. 1-p. 7.

* cited by examiner

ELECTRONIC ATOMIZING DEVICE AND ATOMIZER AND SUCTION NOZZLE ASSEMBLY THEREOF

CROSS REFERENCE TO RELATED APPLICATION

The present invention is based upon and claims the benefit of priority from the prior Chinese Patent Application No. 201920673346.6 filed on May 8, 2019; the entirety of the above-mentioned patent application is hereby incorporated by reference herein and made a part of this specification.

TECHNICAL FIELD

The present invention relates to the technical field of atomization, and more specifically, to an electronic atomizing device and an atomizer and a suction nozzle assembly thereof.

BACKGROUND

Electronic atomizing devices are also known as electronic cigarettes or virtual cigarettes. With similar appearance and flavor to conventional cigarettes, the electronic atomizing devices are generally free of harmful chemicals like tar or aerosol in the cigarettes.

An electronic atomizing device mainly includes a suction nozzle assembly, an atomizing body, and a power supply assembly. Conventionally, the power supply assembly includes an operation switch such as a button switch for controlling a power supply on or off.

In the conventional electronic atomizing device, a suction nozzle in the suction nozzle assembly is generally flat to comply with a habit of suction by a human mouth, and the operation switch of the power supply assembly is generally fixed thereon. Generally, the suction nozzle is not rotatable relative to the power supply assembly. The operation switch may not be on a same plane as the suction nozzle/a human eye, which is inconvenient to manually operate the operation switch. A user may need to take the suction nozzle away from the mouth before operating the operation switch, thereby bringing bad suction experience to the user.

SUMMARY

A technical problem to be solved in the present invention is to provide an improved electronic atomizing device and an atomizer and a suction nozzle assembly thereof. In the electronic atomizing device, a suction nozzle is rotatable relative to a power supply assembly, so that an operation switch can be rotated from an initial position to a position suitable for an operation.

A technical solution adopted by the present invention to solve the technical problem is to construct a suction nozzle assembly including:

a fixing base, wherein the fixing base includes a first longitudinal axis;

a suction nozzle, wherein the suction nozzle includes a second longitudinal axis parallel to or coincident with the first longitudinal axis; the suction nozzle includes a first end and a second end away from the first end, and the second end has a non-circular cross section; and a connecting member, wherein one end of the connecting member is mounted to the suction nozzle, another end is mounted to the fixing base, such that the suction nozzle is disposed on the fixing base via the first end, and is capable of rotating around the second longitudinal axis relative to the fixing base.

In some embodiments, the suction nozzle, the fixing base, and the connecting member are coaxially assembled, and the suction nozzle is capable of rotating 360 degrees around a center axis of the fixing base.

In some embodiments, the suction nozzle, the fixing base, and the connecting member define a first vent hole, a second vent hole, and a third vent hole extending therethrough respectively, and the first vent hole, the second vent hole, and the third vent hole are coaxially arranged and communicate with each other.

In some embodiments, an inner periphery of the fixing base is provided with a first flange extending inwards; the connecting member extends rotatably through an inner hole of the first flange into the suction nozzle, and is fixedly connected to the suction nozzle; and an outer periphery of the connecting member is provided with a second flange extending outwards; an end surface of the second flange towards the second end of the suction nozzle rotatably abuts against an end surface of the first flange.

In some embodiments, the first vent hole includes a second hole and a third hole that are sequentially connected, an aperture of the second hole is larger than an aperture of the third hole, one end of the fixing base is rotatably fit in the second hole, and one end of the connecting member is fixedly fit in the third hole.

In some embodiments, the first vent hole includes a first hole, a second hole, and a third hole that are sequentially connected, apertures of the first hole, the second hole, and the third hole are sequentially decreased; a first sealing member is disposed between an outer wall of the fixing base and an inner wall of the first hole.

In some embodiments, the connecting member includes a first connecting section, a second connecting section, and a third connecting section that are sequentially connected, and outer diameters of the first connecting section, the second connecting section, and the third connecting section are sequentially decreased; the second flange is defined around an outer periphery of the first connecting section, the second connecting section is rotatably fit in the inner hole of the first flange, the third connecting section is fixedly fit in the third hole, and a space is defined between an end surface of the fixing base towards the second end of the suction nozzle and an end surface of the second hole towards the third hole.

In some embodiments, an axial length of the third connecting section is larger than an axial length of the first connecting section and an axial length of the second connecting section respectively, and the third connecting section is interference fit in the third hole.

In some embodiments, the second end of the suction nozzle is flat.

The present invention further provides an atomizer, including an atomizing body and the above suction nozzle assembly, wherein the atomizing body includes a first housing and an atomizing assembly, and the fixing base is disposed on the first housing; an atomizing cavity and a liquid storage cavity are respectively defined in the first housing, the atomizing assembly is disposed in the atomizing cavity and fluidly connected to the liquid storage cavity.

In some embodiments, the fixing base includes a first portion extending into the suction nozzle, a third portion extending into the first housing, and a second portion extending out of the suction nozzle and the first housing.

In some embodiments, a baffle annulus extending outwards is provided around an outer periphery of the second portion, an inner diameter of the baffle annulus is larger than an outer diameter of the second portion, and a second sealing member is disposed between inner walls of the baffle annulus and the first housing and outer walls of the second portion and the third portion.

In some embodiments, the atomizing body further includes a vent pipe disposed in the first housing, the atomizing cavity is defined in the vent pipe, the liquid storage cavity is defined between the first housing and the vent pipe, the vent pipe extends through the first housing into the fixing base, and a gap is defined between an end surface of the vent pipe towards the suction nozzle assembly and an end surface of the connecting member towards the fixing base.

In some embodiments, a third sealing member is disposed between an outer wall of the vent pipe and an inner wall of the fixing base.

The present invention further provides an electronic atomizing device, including an atomizing body, a power supply assembly, and the above suction nozzle assembly, wherein the atomizing body includes a first housing and an atomizing assembly, and the fixing base is disposed on the first housing; an atomizing cavity and a liquid storage cavity are respectively defined in the first housing, the atomizing assembly is disposed in the atomizing cavity and fluidly connected to the liquid storage cavity; the power supply assembly includes an operation switch, and the power supply assembly is disposed at an end of the atomizing body away from the suction nozzle assembly, and is electrically connected to the atomizing assembly.

In some embodiments, the power supply assembly is detachably connected to the atomizing body, and a rotation friction force between the power supply assembly and the atomizing body is larger than that between the suction nozzle and the fixing base.

In some embodiments, the power supply assembly is threadedly connected to the atomizing body.

Implementation of the present invention has at least the following beneficial effects: the suction nozzle is rotatably connected to the power supply assembly, therefore when a user holds the suction nozzle in a mouth at a comfortable angle, the suction nozzle can be relatively rotated from an initial position to an operation position where the operation switch is within a sight range of a human eye, so that the operation switch is convenient to operate.

BRIEF DESCRIPTION OF THE DRAWINGS

The present invention will now be further described with reference to the accompanying drawings and embodiments, in the accompanying drawings.

DETAILED DESCRIPTION

In order to render a more apparent understanding of technical features, objects and effects of the present invention, specific embodiments thereof will be described in detail with reference to the accompanying drawings.

Figure 1:
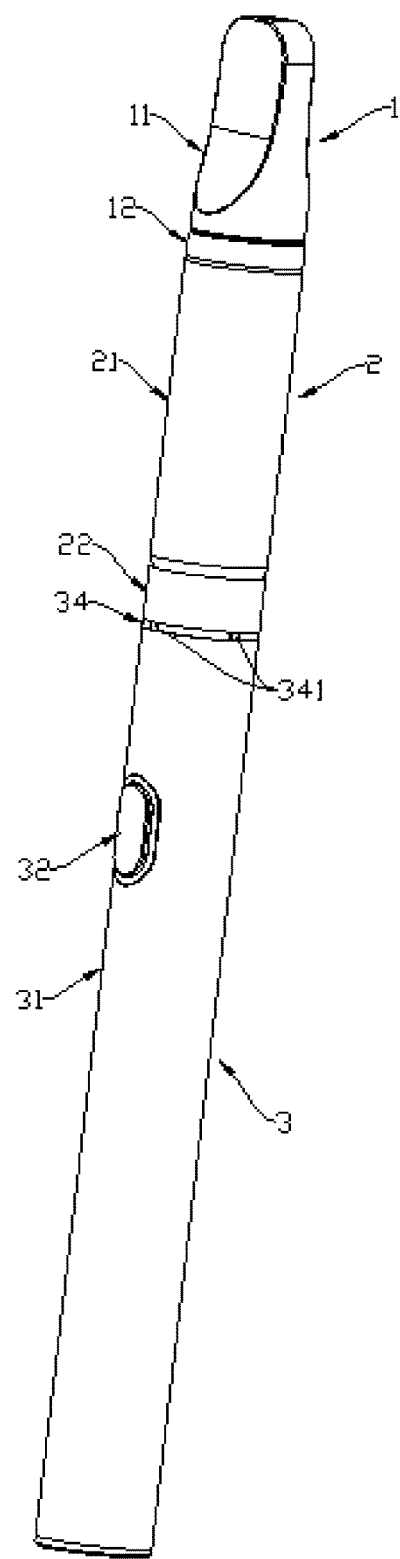
FIG. 1 is a schematic structural diagram of an electronic atomizing device according to an embodiment of the present invention.
Figure 2:
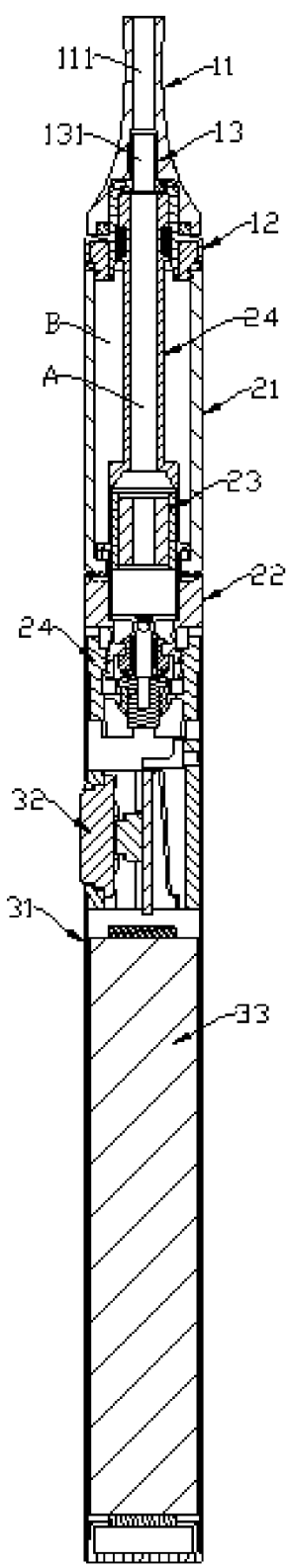
FIG. 2 is a cross-sectional diagram of the electronic atomizing device according to the embodiment of the present invention.

As shown in FIG. 1 and FIG. 2, an electronic atomizing device in an embodiment of the present invention includes an atomizing body 2, a suction nozzle assembly 1 and a power supply assembly 3. The suction nozzle assembly 1 and the power supply assembly 3 are respectively disposed on two ends of the atomizing body 2. The electronic atomizing device may be used as an electronic cigarette, or a medical atomizer or the like.

The atomizing body 2 may include a first housing 21 and an atomizing assembly 23. An atomizing cavity A and a liquid storage cavity B are respectively defined in the first housing 21. The liquid storage cavity B is used for storing liquid such as smoke liquid or medicinal liquid. The atomizing assembly 23 is disposed in the atomizing cavity A, and is in fluid communication with the liquid storage cavity B.

The power supply assembly 3 may include a second housing 31 and a battery 33 disposed in the second housing 31. The second housing 31 is provided with an operation switch 32 such as a button switch for controlling a power supply on or off. When the power supply assembly 3 and the atomizing body 2 are assembled, the power supply assembly 3 can supply power to the atomizing assembly 23, to heat and atomize smoke liquid for a user to draw.

The suction nozzle assembly 1 may include a suction nozzle 11, a fixing base 12, and a connecting member 13. The suction nozzle assembly 1 is disposed on the first housing 21 via the fixing base 12. The suction nozzle 11 includes a first end and a second end away from the first end, and the suction nozzle 11 is rotatably disposed on the fixing base 12 via the first end. The second end of the suction nozzle 11 has a non-circular cross section. Different mouthfeels and suction experiences can be obtained when the suction nozzle 11 is hold in a mouth at different angles. In this embodiment, the second end of the suction nozzle 11 applies a flat design. The flat nozzle is able to fit lips better, and to render smoke more concentrated, thereby to achieve a better smoking experience.

The fixing base 12, the atomizing body 2, and the power supply assembly 3 are relatively fixed, and the suction nozzle 11 is rotatable relative to the fixing base 12. The operation switch 32 is fixed on the second housing 31. Therefore, when the user holds the suction nozzle 11 in the mouth at a comfortable angle, the suction nozzle 11 is able to rotate relatively from an initial position to an operation position, and the operation switch 32 is within a sight range of a human eye at the operation position, so that the operation switch 32 is convenient to operate.

Figure 3:
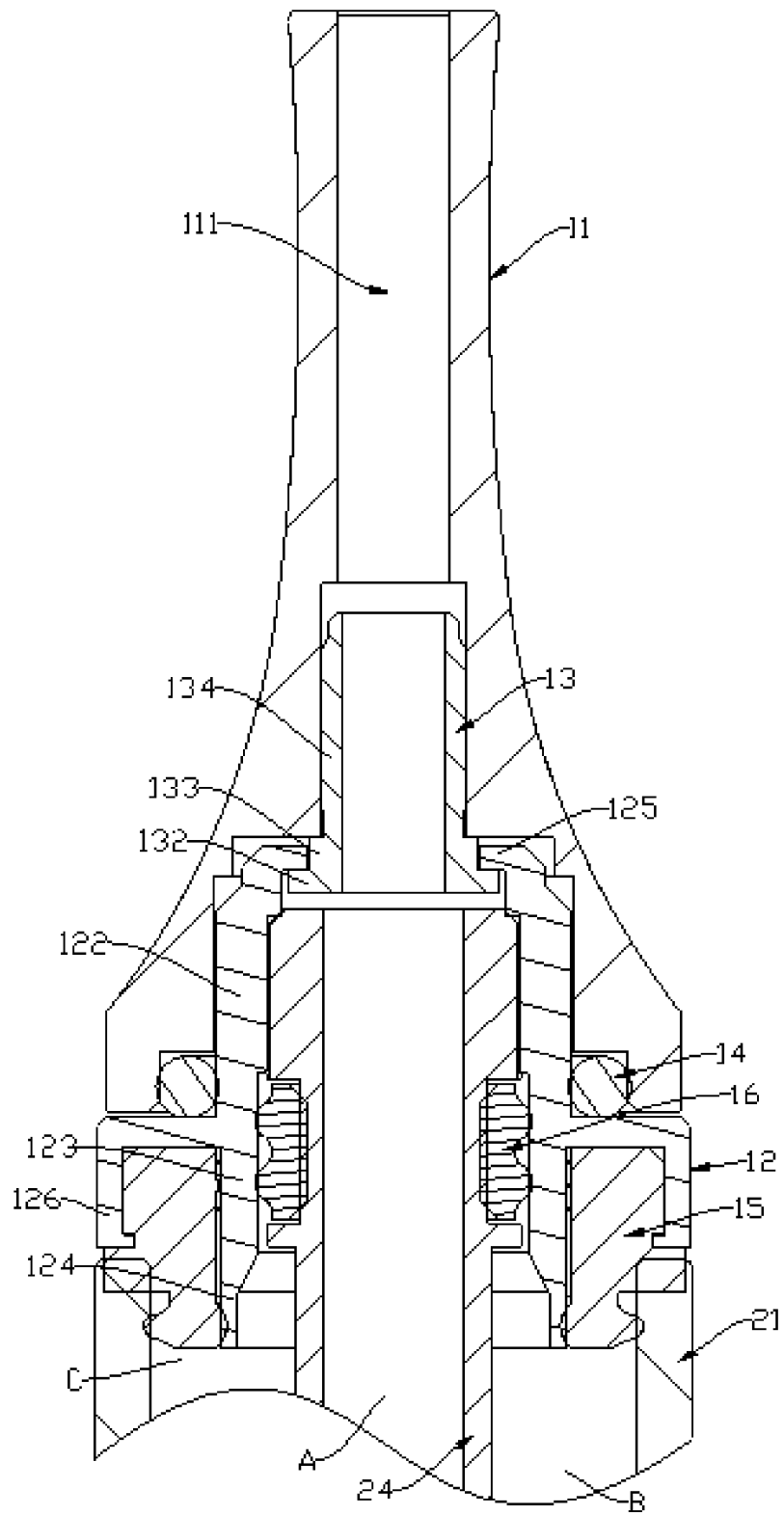
FIG. 3 is a schematic diagram of a suction nozzle assembly and an atomizing body when assembling according to the embodiment of the present invention.
Figure 4:
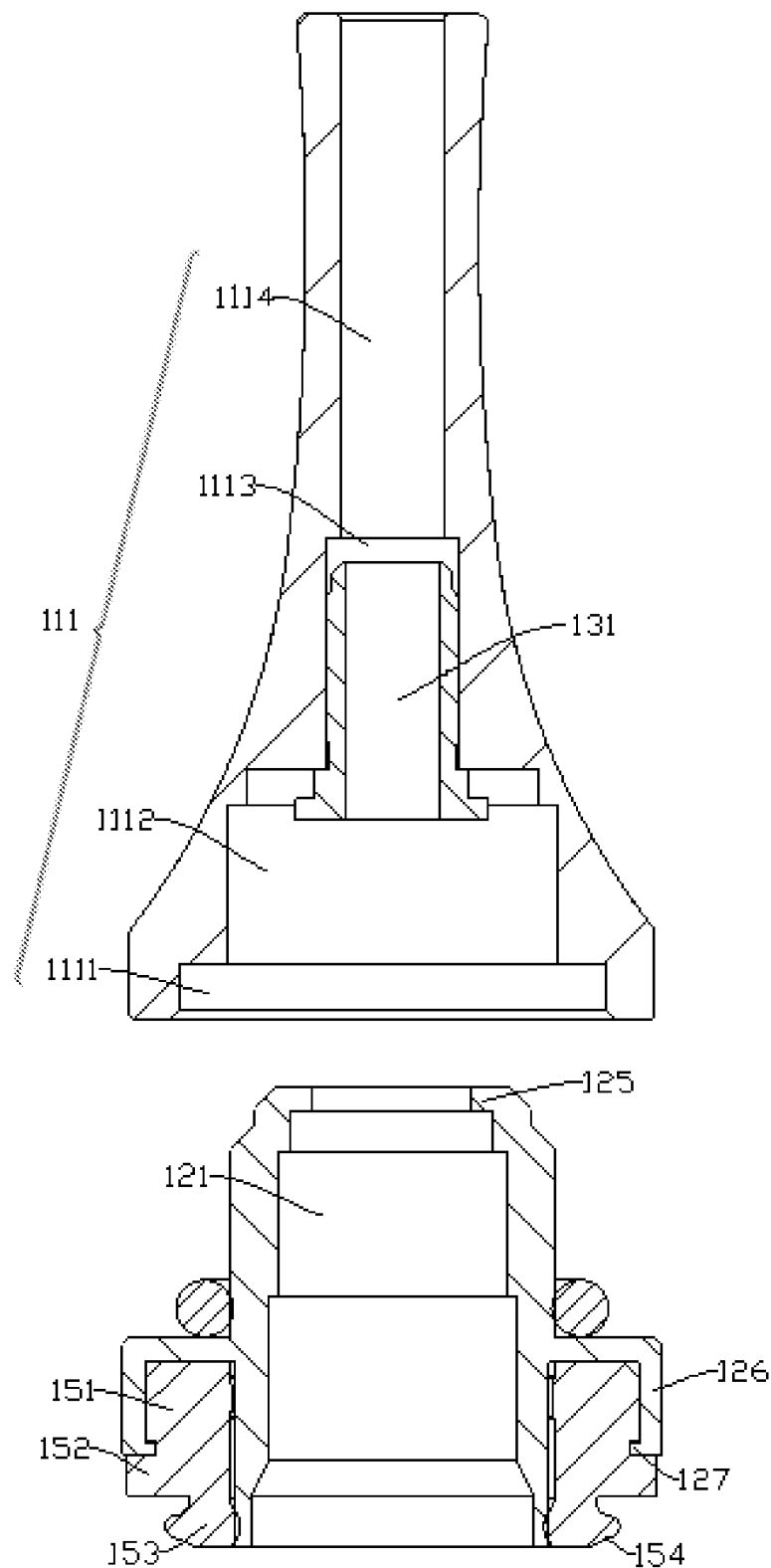
FIG. 4 is an exploded diagram of the suction nozzle assembly according to the embodiment of the present invention.

As shown in FIG. 3 and FIG. 4, the fixing base 12 includes a first longitudinal axis, and the suction nozzle 11 includes a second longitudinal axis parallel to or coincident with the first longitudinal axis. One end of the connecting member 13 is mounted to the suction nozzle 11, and another end of the connecting member 13 is mounted to the fixing base 12, so that the suction nozzle 11 is disposed on the fixing base 12 via the first end, and is capable of rotating around the second longitudinal axis relative to the fixing base 12.

In this embodiment, the suction nozzle 11, the fixing base 12, and the connecting member 13 are coaxially assembled. One end of the connecting member 13 is fixedly disposed in the suction nozzle 11, and another end of the connecting member 13 is rotatably disposed in the fixing base 12. An inner periphery of the fixing base 12 is provided with a first flange 125 extending inwards. The connecting member 13 extends rotatably through an inner hole of the first flange 125 into the suction nozzle 11, and is fixedly connected to the suction nozzle 11. An outer periphery of the connecting member 13 is provided with a second flange extending outwards. An end surface of the second flange towards the second end of the suction nozzle 11 rotatably abuts against an end surface of the first flange 125. The connecting member 13 is capable of rotating 360 degrees in the inner hole of the first flange 125, so that the suction nozzle 11 is capable of rotating 360 degrees around a center axis of the fixing base 12. Alternatively, in another embodiment, one end of the connecting member 13 may be rotatably disposed in the suction nozzle 11, and another end of the connecting member 13 may be fixedly disposed in the fixing base 12, so that the suction nozzle 11 is capable of rotating relative to the fixing base 12.

The fixing base 12, the connecting member 13, and the first end of the suction nozzle 11 may be cylindrical respectively. The second end of the suction nozzle 11 may be flat. The suction nozzle 11, the fixing base 12, and the connecting member 13 define a first vent hole 111, a second vent hole 121, and a third vent hole 131 extending therethrough respectively. The first vent hole 111, the second vent hole 121, and the third vent hole 131 are fluidly communicated with each other, and may be coaxially disposed with the suction nozzle 11, the fixing base 12, and the connecting member 13.

One end of the fixing base 12 may extend into the first vent hole 111 of the suction nozzle 11. The first flange 125 may extend inwardly from an inner periphery of an end of the fixing base 12 towards the connecting member 13. A first sealing member 14 may be disposed between an outer wall of the fixing base 12 and an inner wall of the first vent hole 111, so that the fixing base 12 is sealedly connected to the suction nozzle 11, to prevent a leakage of smoke through a fitting gap between the suction nozzle 11, the fixing base 12, and the connecting member 13. In another embodiment, the first end of the suction nozzle 11 may extend into the fixing base 12, and a sealing member is disposed between an outer wall of the suction nozzle 11 and an inner wall of the fixing base 12, to achieve sealing.

The first vent hole 111 may be a stepped hole, and may include a first hole 1111, a second hole 1112, a third hole 1113, and a fourth hole 1114 that are sequentially connected. Apertures of the first hole 1111, the second hole 1112, the third hole 1113, and the fourth hole 1114 are sequentially decreased. The first hole 1111 and the fourth hole 1114 are respectively disposed at the first end and the second end of the suction nozzle 11, to provide mounting space for the connecting member 13, the fixing base 12, and the first sealing member 14.

The fixing base 12 may be rotatably disposed in the second hole 1112 in a gap fitting manner. The connecting member 13 may be fixedly disposed in the third hole 1113 through riveting, gluing, interference-fitting, or the like. The first sealing member 14 is disposed between the outer wall of the fixing base 12 and an inner wall of the first hole 1111. The inner wall of the first hole 1111 can press the first sealing member 14, so that the first sealing member 14 is in close abutment with the outer wall of the fixing base 12 and the inner wall of the first hole 1111 closely respectively, to achieve a better sealing effect.

The connecting member 13 may include a first connecting section 132, a second connecting section 133, and a third connecting section 134 that are sequentially connected. And outer diameters of the first connecting section 132, the second connecting section 133, and the third connecting section 134 are sequentially decreased. The second flange is defined around an outer periphery of the connecting section 132, and rotatably abuts against an end surface of the first flange 125.

The second connecting section 133 is rotatably fit in the inner hole of the first flange 125. A stepped surface defined between the second connecting section 133 and the third connecting section 134 may abut against a stepped surface defined between the second hole 1112 and the third hole 1113. An axial length of the second connecting section 133 is larger than an axial length of the first flange 125, so that a space is defined between an end surface of the fixing base 12 which is towards the second end of the suction nozzle 11 and the stepped surface defined between the second connecting section 133 and the third connecting section 134. Thereby a space is provided for the suction nozzle 11 to rotate, and a rotation friction force between the suction nozzle 11 and the fixing base 12 is reduced.

An axial length of the third connecting section 134 is larger than an axial length of the first connecting section 132 and an axial length of the second connecting section 133 respectively, so that a connection strength between the connecting member 13 and the suction nozzle 11 can be ensured when the third connecting section 134 is fixedly disposed in the third hole 1113 through interference-fitting or the like. Thereby, it is not easy for the connecting member 13 to fall off. A guiding portion such as an inclined transition surface or an arc transition surface may be disposed on an end portion of the third connecting section 134 which is away from the second connecting section 133, to enable the third connecting section 134 to be inserted into the third hole 1113 easily.

When assembling the suction nozzle assembly 1, the fixing base 12 is inserted into the second hole 1112 of the suction nozzle 11 from the first end of the suction nozzle 11, the connecting member 13 is inserted into the third hole 1113 in the suction nozzle 11 from an end of the fixing base 12 which is away from the suction nozzle 11. The stepped surface defined between the second connecting section 133 and the third connecting section 134 abuts against the stepped surface defined between the second hole 1112 and the third hole 1113 to achieve positioning. An end portion of the third connecting section 134 of the connecting member 13 which extends out of the first flange 125 is riveted in the third hole 1113 of the suction nozzle 11.

The atomizing body 2 may include a first housing 21 and a vent pipe 24 extending in the first housing 21. The first housing 21 and the vent pipe 24 may be cylindrical respectively. The atomizing cavity A is defined in the vent pipe 24, and the liquid storage cavity B is defined between the first housing 21 and the vent pipe 24. The atomizing cavity A is fluidly communicated with the first vent hole 111, the second vent hole 121, and the third vent hole 131 in the suction nozzle assembly 1, to define a aerosol channel.

The fixing base 12 may be detachably disposed at an end of the first housing 21. A rotation friction force between the fixing base 12 and the first housing 21 is larger than a rotation friction force between the suction nozzle 11 and the fixing base 12. An end portion of the first housing 21 which is towards the fixing base 12 may define a liquid injection port C for injecting liquid into the liquid storage cavity B, so that the atomizer can be reused.

The fixing base 12 may include a first portion 122 extending into the suction nozzle 11, a third portion 124 extending into the first housing 21, and a second portion 123 extending out of the suction nozzle 11 and the first housing 21. An outer diameter of the first portion 122, an outer diameter of the second portion 123, and an outer diameter of the third portion 124 may be equal to each other and slightly less than the aperture of the second hole 1112, so that the first portion 122 is clearance fit in the second hole 1112.

A baffle annulus 126 extending outwards is provided around an outer periphery of the second portion 123. An outer diameter of the baffle annulus 126 may be equal to an outer diameter of the first housing 21. An inner diameter of the baffle annulus 126 is larger than an outer diameter of the second portion 123. A second sealing member 15 is disposed between inner walls of the baffle annulus 126 and the first housing 21 and outer walls of the second portion 123 and the third portion 124.

The second sealing member 15 may include a first sealing portion 151, a second sealing portion 152, and a third sealing portion 153. The first sealing portion 151 is disposed between the inner wall of the baffle annulus 126 and the outer wall of the second portion 123. The second sealing portion 152 is disposed at an end of the first sealing portion 151 which is towards the liquid storage cavity B, and an outer diameter of the first sealing portion 151 is larger than an inner diameter of the baffle annulus 126 and an inner diameter of the first housing 21 respectively, to achieve a sealing between an end portion of the fixing base 12 and an end portion of the first housing 21. An inner periphery of an end of the baffle annulus 126 which is towards the first housing 21 is provided with a third flange 127 extending inwards, so that a contact area with the second sealing portion 152 is increased, and a squeezing force applied to the second sealing portion 152 is increased, to achieve a better sealing performance. Besides, the second sealing member 15 can be prevented from falling off the fixing base 12, when the suction nozzle assembly 1 is detached from the atomizing body 2.

The third sealing portion 153 is disposed at an end of the second sealing portion 152 which is towards the liquid storage cavity B, and an outer diameter of the third sealing portion 153 is less than the inner diameter of the first housing 21. An outer periphery of an end of the third sealing portion 153 which is away from the second sealing portion 152 is provided with a guiding portion 154 extending outwards. An outer diameter of the guiding portion 154 is larger than the inner diameter of the first housing 21. The guiding portion 154 may be an inclined transition surface or an arc transition surface. The third sealing portion 153 and the guiding portion 154 can ensure a tight fit between the outer wall of the third portion 124 and the inner wall of the first housing 21, and block the liquid into the liquid storage cavity B as much as possible, to reduce or prevent the liquid from contacting the second sealing portion 152, thereby preventing the liquid from being adhered to the second sealing portion 152. If too much liquid is adhered to the second sealing portion 152, when assembling the suction nozzle assembly 1 and the atomizing body 2, the liquid adhered to the second sealing portion 152 will be squeezed out of the atomizer. Consequently, an outer surface of the atomizer is polluted.

The vent pipe 24 may extend through the first housing 21 into the fixing base 12. A gap may be defined between an end surface of the vent pipe 24 which is towards the suction nozzle assembly 1 and an end surface of the connecting member 13 which is towards the fixing base 12, to provide a rotating space for the suction nozzle 11.

The outer wall of the vent pipe 24 sealingly fits with the inner wall of the fixing base 12, to block the liquid into the liquid storage cavity B. Preferably, a third sealing member 16 may be disposed between the outer wall of the vent pipe 24 and the inner wall of the fixing base 12, to achieve sealing at the position.

Figure 5:
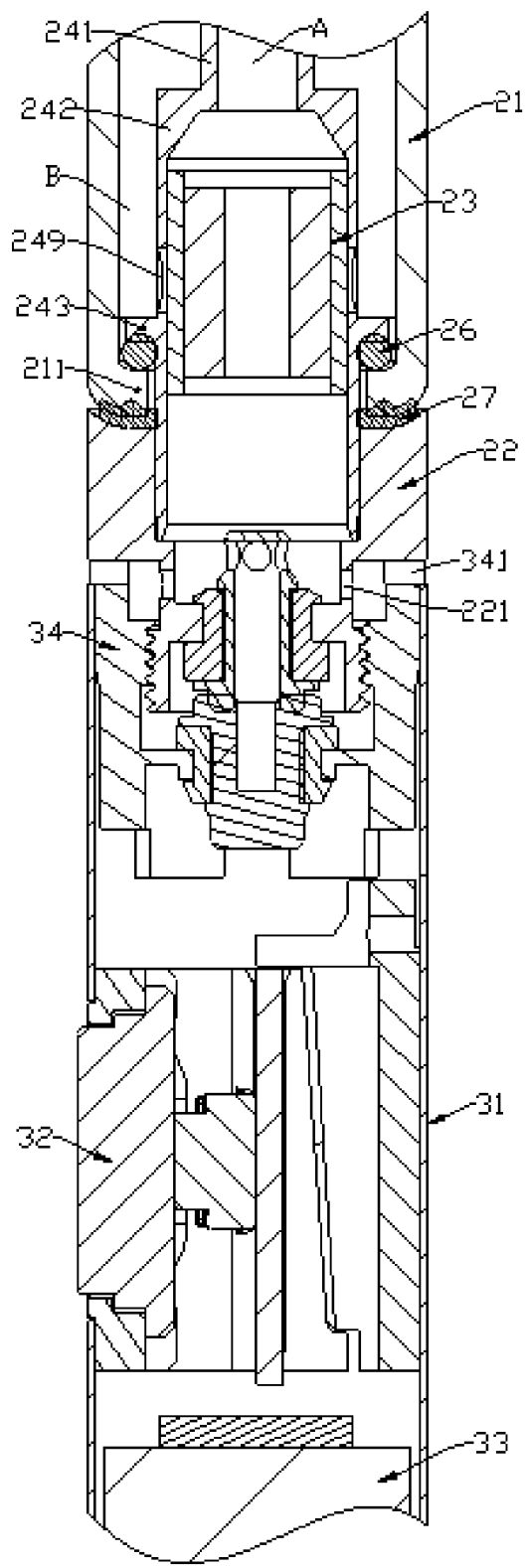
FIG. 5 is a schematic diagram of the atomizing body and a power supply assembly when assembling according to the embodiment of the present invention.
Figure 6:
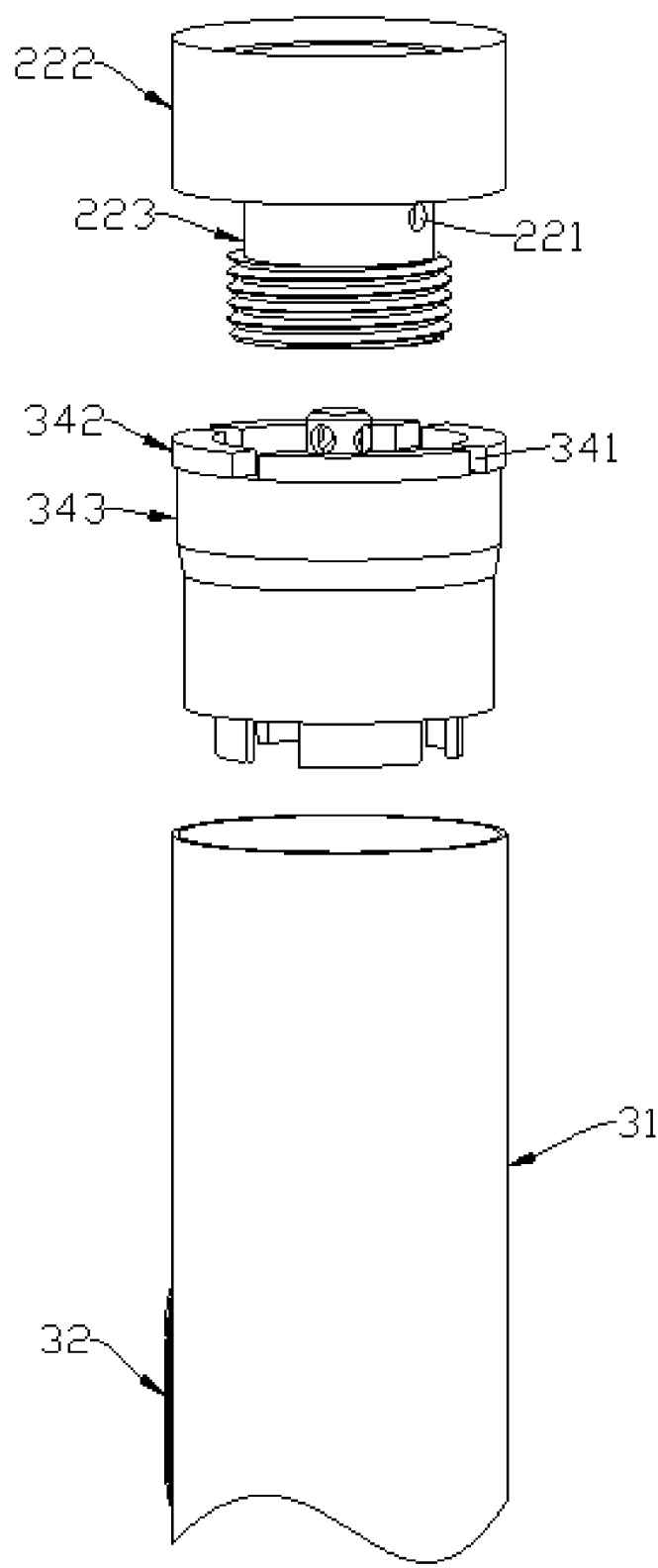
FIG. 6 is an exploded diagram of a first connecting assembly and the power supply assembly according to the embodiment of the present invention.

As shown in FIG. 5 and FIG. 6, the atomizing body 2 and the power supply assembly 3 may be detachably connected together, and a rotation friction force between the atomizing body 2 and the power supply assembly 3 is larger than that between the suction nozzle 11 and the fixing base 12. The atomizing body 2 defines at least one first air inlet 221. The power supply assembly 3 defines at least one second air inlet 341. The at least one second air inlet 341 and the at least one first air inlet 221 are fluidly communicated for air inlet.

In this embodiment, the atomizing body 2 may further include a first connecting assembly 22. The first connecting assembly 22 is disposed at an end of the first housing 21 which is away from the fixing base 12. The first connecting assembly 22 may be detachably disposed on the power supply assembly 3 through a threaded connection or the like. The vent pipe 24 may extend through the first housing 21 into the first connecting assembly 22, and is fixedly connected to the first connecting assembly 22.

An inner periphery of an end of the first housing 21 which is towards the first connecting assembly 22 is provided with a fourth flange 211 extending inwards. A fifth flange 243 extending outwards is provided around an outer periphery of the vent pipe 24. The fifth flange 243 is disposed in the liquid storage cavity B, and the fifth flange 243 and the first connecting assembly 22 abut against and sealing fit with an inner side and an outer side of the fourth flange 211 respectively. Preferably, a fourth sealing member 26 is disposed between the fifth flange 243 and the fourth flange 211, and a fifth sealing member 27 is disposed between the first connecting assembly 22 and the fourth flange 211, to improve a sealing performance.

The vent pipe 24 may include a first pipe portion 241 and a second pipe portion 242, and an inner diameter and an outer diameter of the second pipe portion 242 are respectively larger than that of the first pipe portion 241. An end portion of the first pipe portion 241 which is away from the second pipe portion 242 is correspondingly connected to the suction nozzle assembly 1, and an end portion of the second pipe portion 242 which is away from the first pipe portion 241 is correspondingly connected to the first connecting assembly 22.

The atomizing assembly 23 may be disposed in the second pipe portion 242, and a liquid inlet 249 fluidly communicated with the liquid storage cavity B is defined on a side wall of the second pipe portion 242. The liquid will be adsorbed by the atomizing assembly 23 when entering the second pipe portion 242 via the liquid inlet 249. The adsorbed liquid will be heated and atomized to aerosol by the atomizing assembly 23, and the aerosol flows to the suction nozzle 11 through the first pipe portion 241. The vent pipe 24 has a structure with two ends having different inner diameters and different outer diameters, thereby a mounting space of the atomizing assembly 23 is provided, and a space of the liquid storage cavity B increased, thereby facilitating an increase in a liquid storage of the atomizer.

When assembling, the vent pipe 24 is inserted into the first housing 21 from an end which is towards the suction nozzle 11, and the fifth flange 243 abuts against the fourth flange 211 to achieve positioning. An end portion of the second pipe portion 242 of the vent pipe 24 extending out of the fourth flange 211 is riveted to the first connecting assembly 22.

In this embodiment, the power supply assembly 3 may include a second housing 31, a second connecting assembly 34, an operation switch 32, and a battery 33. The operation switch 32 is disposed on the second housing 31, and may include a button switch in some embodiments. The battery 33 may be disposed in the second housing 31, and may include a cylindrical lithium battery in some embodiments. A space for air flowing is defined between an outer wall of the battery 33 and an inner wall of the second housing 31.

The second connecting assembly 34 is disposed at an end of the second housing 31 which is towards the first connecting assembly 22. The atomizing body 2 and the power supply assembly 3 are assembled via the first connecting assembly 22 and second connecting assembly 34.

The first connecting assembly 22 may include a first connecting portion 222 extending out of the second connecting assembly 34 and a second connecting portion 223 extending into the second connecting assembly 34. The second connecting assembly 34 may include a third connecting portion 342 extending out of the second housing 31 and a fourth connecting portion 343 extending into the second housing 31. The first air inlet 221 and the second air inlet 341 may be respectively defined on the second connecting portion 223 and the third connecting portion 342. Furthermore, the first connecting assembly 22 may include a smooth portion connected to the first connecting portion 222 and a threaded portion away from the first connecting portion 222, and the first air inlet 221 may be defined on the smooth portion.

It is noteworthy that, the above-mentioned technical features can be used in any combination without restriction.

The disclosure described above of the present invention is illustrative but not restrictive scope of the present invention. Any equivalent structure, or equivalent process transformation, or directly or indirectly usage in other related technical field, all those be made in the same way are included within the protection scope of the present invention.

What is claimed is:

1. A suction nozzle assembly, comprising:
   a fixing base;
   a suction nozzle, wherein the suction nozzle comprises a first end and a second end away from the first end; and
   a connecting member, wherein one end of the connecting member is mounted to the suction nozzle, another end is mounted to the fixing base, such that the suction nozzle is disposed on the fixing base via the first end, and is capable of rotating relative to the fixing base, wherein the suction nozzle, the fixing base, and the connecting member define a first vent hole, a second vent hole, and a third vent hole extending therethrough respectively, and the first vent hole, the second vent hole, and the third vent hole are coaxially arranged and communicate with each other;
   an inner periphery of the fixing base is provided with a first flange extending inwards; the connecting member extends rotatably through an inner hole of the first flange into the suction nozzle, and is fixedly connected to the suction nozzle; and
   an outer periphery of the connecting member is provided with a second flange extending outwards; an end surface of the second flange towards the second end of the suction nozzle rotatably abuts against an end surface of the first flange.

2. The suction nozzle assembly according to claim 1, wherein the suction nozzle, the fixing base, and the connecting member are coaxially assembled; the suction nozzle is capable of rotating 360 degrees around a center axis of the fixing base, and the second end of the suction nozzle is flat.

3. The suction nozzle assembly according to claim 1, wherein the first vent hole comprises a first hole, a second hole, and a third hole that are sequentially connected, apertures of the first hole, the second hole, and the third hole are sequentially decreased; one end of the fixing base is rotatably fit in the second hole, and one end of the connecting member is fixedly fit in the third hole; a first sealing member is disposed between an outer wall of the fixing base and an inner wall of the first hole.

4. The suction nozzle assembly according to claim 3, wherein the connecting member comprises a first connecting section, a second connecting section, and a third connecting section that are sequentially connected, and outer diameters of the first connecting section, the second connecting section, and the third connecting section are sequentially decreased; the second flange is defined around an outer periphery of the first connecting section, the second connecting section is rotatably fit in the inner hole of the first flange, the third connecting section is fixedly fit in the third hole, and a space is defined between an end surface of the fixing base towards the second end of the suction nozzle and an end surface of the second hole towards the third hole.

5. The suction nozzle assembly according to claim 4, wherein an axial length of the third connecting section is larger than an axial length of the first connecting section and an axial length of the second connecting section respectively, and the third connecting section is interference fit in the third hole.

6. An atomizer, comprising an atomizing body and a suction nozzle assembly, wherein the atomizing body comprises a first housing and an atomizing assembly, and the suction nozzle assembly comprises a fixing base, a suction nozzle, and a connecting member;
   an atomizing cavity and a liquid storage cavity are respectively defined in the first housing, the atomizing assembly is disposed in the atomizing cavity and fluidly connected to the liquid storage cavity;
   the fixing base is disposed on the first housing; the suction nozzle comprises a first end and a second end away from the first end; one end of the connecting member is mounted to the suction nozzle, another end is mounted to the fixing base, such that the suction nozzle is disposed on the fixing base via the first end, and is capable of rotating relative to the fixing base, wherein the suction nozzle, the fixing base, and the connecting member define a first vent hole, a second vent hole, and a third vent hole extending therethrough respectively, and the first vent hole, the second vent hole, and the third vent hole are coaxially arranged and communicate with each other;
   an inner periphery of the fixing base is provided with a first flange extending inwards; the connecting member extends rotatably through an inner hole of the first flange into the suction nozzle, and is fixedly connected to the suction nozzle; and
   an outer periphery of the connecting member is provided with a second flange extending outwards; an end surface of the second flange towards the second end of the suction nozzle rotatably abuts against an end surface of the first flange.

7. The atomizer according to claim 6, wherein the fixing base comprises a first longitudinal axis, the suction nozzle comprises a second longitudinal axis parallel to or coincident with the first longitudinal axis, and the suction nozzle is capable of rotating relative to the fixing base around the second longitudinal axis; the second end of the suction nozzle has a non-circular cross section.

8. The atomizer according to claim 6, wherein the fixing base comprises a first portion extending into the suction nozzle, a third portion extending into the first housing, and a second portion extending out of the suction nozzle and the first housing;
a baffle annulus extending outwards is provided around an outer periphery of the second portion, an inner diameter of the baffle annulus is larger than an outer diameter of the second portion, and a second sealing member is disposed between inner walls of the baffle annulus and the first housing and outer walls of the second portion and the third portion.

9. The atomizer according to claim 8, wherein the atomizing body further comprises a vent pipe disposed in the first housing, the atomizing cavity is defined in the vent pipe, the liquid storage cavity is defined between the first housing and the vent pipe, the vent pipe extends through the first housing into the fixing base, and a gap is defined between an end surface of the vent pipe towards the suction nozzle assembly and an end surface of the connecting member towards the fixing base.

10. The atomizer according to claim 6, wherein the first vent hole comprises a second hole and a third hole that are sequentially connected, an aperture of the second hole is larger than an aperture of the third hole, one end of the fixing base is rotatably fit in the second hole, and one end of the connecting member is fixedly fit in the third hole.

11. The atomizer according to claim 10, wherein the connecting member comprises a first connecting section, a second connecting section, and a third connecting section that are sequentially connected, and outer diameters of the first connecting section, the second connecting section, and the third connecting section are sequentially decreased; the second flange is defined around an outer periphery of the first connecting section, the second connecting section is rotatably fit in the inner hole of the first flange, the third connecting section is fixedly fit in the third hole, and a space is defined between an end surface of the fixing base towards the second end of the suction nozzle and an end surface of the second hole towards the third hole.

12. The atomizer according to claim 6, wherein the suction nozzle, the fixing base, and the connecting member are coaxially arranged; the suction nozzle is capable of rotating 360 degrees around a center axis of the fixing base, and the second end of the suction nozzle is flat.

13. An electronic atomizing device, comprising an atomizing body, a power supply assembly, and a suction nozzle assembly, wherein the atomizing body comprises a first housing and an atomizing assembly, an atomizing cavity and a liquid storage cavity are respectively defined in the first housing, the atomizing assembly is disposed in the atomizing cavity and fluidly connected to the liquid storage cavity;
the suction nozzle assembly comprises a fixing base, a suction nozzle, and a connecting member; the fixing base is disposed on the first housing; the suction nozzle comprises a first end and a second end away from the first end; one end of the connecting member is mounted to the suction nozzle, another end is mounted to the fixing base, such that the suction nozzle is disposed on the fixing base via the first end, and is capable of rotating relative to the fixing base;
the power supply assembly comprises an operation switch, and the power supply assembly is disposed at an end of the atomizing body away from the suction nozzle assembly, and is electrically connected to the atomizing assembly, wherein the suction nozzle, the fixing base, and the connecting member define a first vent hole, a second vent hole, and a third vent hole extending therethrough respectively, and the first vent hole, the second vent hole, and the third vent hole are coaxially arranged and communicate with each other;
an inner periphery of the fixing base is provided with a first flange extending inwards; the connecting member extends rotatably through an inner hole of the first flange into the suction nozzle, and is fixedly connected to the suction nozzle; and
an outer periphery of the connecting member is provided with a second flange extending outwards; an end surface of the second flange towards the second end of the suction nozzle rotatably abuts against an end surface of the first flange.

14. The electronic atomizing device according to claim 13, wherein the power supply assembly is detachably connected to the atomizing body, and a rotation friction force between the power supply assembly and the atomizing body is larger than that between the suction nozzle and the fixing base.

15. The electronic atomizing device according to claim 13, wherein the first vent hole comprises a second hole and a third hole that are sequentially connected, an aperture of the second hole is larger than an aperture of the third hole, an end of the fixing base is rotatably fit in the second hole, and one end of the connecting member is fixedly fit in the third hole.

16. The electronic atomizing device according to claim 15, wherein the connecting member comprises a first connecting section, a second connecting section, and a third connecting section that are sequentially connected, and outer diameters of the first connecting section, the second connecting section, and the third connecting section are sequentially decreased; the second flange is defined around an outer periphery of the first connecting section, the second connecting section is rotatably fit in the inner hole of the first flange, the third connecting section is fixedly fit in the third hole, and a space is defined between an end surface of the fixing base towards the second end of the suction nozzle and an end surface of the second hole towards the third hole.

* * * * *